United States Patent [19]
Lee et al.

[11] Patent Number: 5,771,902
[45] Date of Patent: Jun. 30, 1998

[54] MICROMACHINED ACTUATORS/SENSORS FOR INTRATUBULAR POSITIONING/STEERING

[75] Inventors: Abraham P. Lee, Walnut Creek; Peter A. Krulevitch, Mountain View; M. Allen Northrup, Berkeley; Jimmy C. Trevino, French Camp, all of Calif.

[73] Assignee: Regents of the University of California, Oakland, Calif.

[21] Appl. No.: 533,426

[22] Filed: Sep. 25, 1995

[51] Int. Cl.⁶ .................................................. A61B 19/00
[52] U.S. Cl. ............................................................ 128/897
[58] Field of Search .................................. 128/630, 772, 128/897, 657; 606/106, 108, 129; 604/156, 159, 271; 607/122

[56] References Cited

U.S. PATENT DOCUMENTS

| | | | |
|---|---|---|---|
| 3,625,200 | 12/1971 | Muller | 128/772 |
| 5,188,111 | 2/1993 | Yates et al. | 128/657 |
| 5,306,261 | 4/1994 | Alliger et al. | 128/657 |
| 5,324,327 | 6/1994 | Cohen | 607/122 |
| 5,358,479 | 10/1994 | Wilson | 128/657 |

*Primary Examiner*—William E. Kamm
*Attorney, Agent, or Firm*—L E. Carnahan; Henry P. Sartorio

[57] ABSTRACT

Micromachined thin film cantilever actuators having means for individually controlling the deflection of the cantilevers, valve members, and rudders for steering same through blood vessels, or positioning same within a blood vessel, for example. Such cantilever actuators include tactile sensor arrays mounted on a catheter or guide wire tip for navigation and tissues identification, shape-memory alloy film based catheter/guide wire steering mechanisms, and rudder-based steering devices that allow the selective actuation of rudders that use the flowing blood itself to help direct the catheter direction through the blood vessel. While particularly adapted for medical applications, these cantilever actuators can be used for steering through piping and tubing systems.

20 Claims, 6 Drawing Sheets

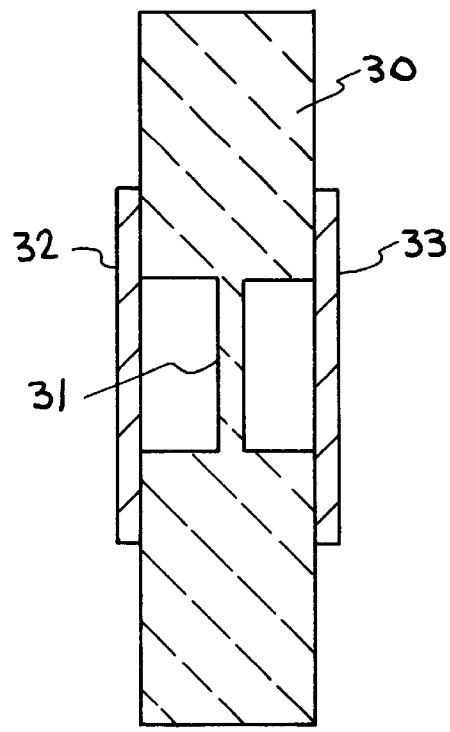
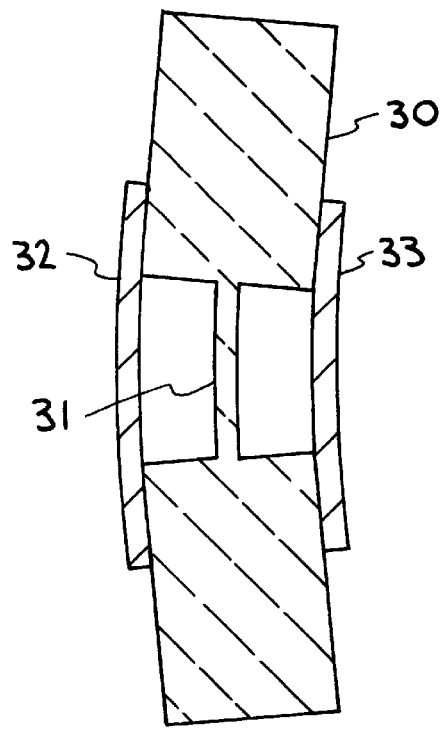
FIG. 3A  FIG. 3B
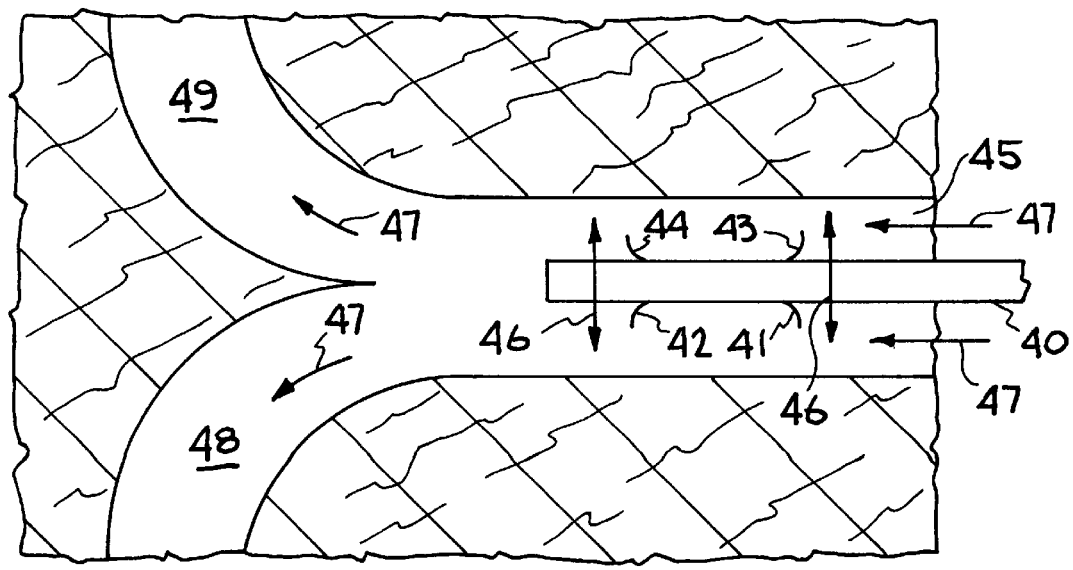
FIG. 4

MICROMACHINED ACTUATORS/SENSORS FOR INTRATUBULAR POSITIONING/STEERING

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to micro-devices particularly to micromachined actuators, and more particularly micromachined cantilever actuators, rudders, microvalves, force sensors, and positioning or steering mechanisms for navigation of endovascular guidewires and/or catheters and redirection of flow in blood vessels.

Present catheter technology, while significantly improving the outcome of severe trauma and congenital diseases is lacking in technological sophistication. Specifically, catheters lack sub-millimeter-sized distal actuators and sensors, adequate embolic and stenting materials and devices, feedback control (both force and tactile), computer-based autonomous control of steering and actuation, and sufficient imaging/therapy coupling. Presently, the catheter-based procedures for cardiological, neurological, and peripheral vessel repairs and treatments require direct, hands-on, continuous manipulation by experienced physicians. Procedures, especially in the neurological field, can be very lengthy (4–6 hours) and extremely tedious.

Some improvements have been made in catheter technology for access; i.e., getting to the site of therapy. Examples are new guidewire materials and reduced sizes of the catheters. As well, there have been new innovations in therapies, especially in the cardiology field. These include balloon angioplasty, laser ablation, stenting, and rotobladers. Most of these are specifically designed to treat arteriosclerosis, and have been minimally successful (restenosis rates of over 35% are common). Most intravascular therapies that are potentially deliverable by catheter methodology are severely limited by the lack of sophistication of the tools themselves, the control of the tools, and the associated technologies such as imaging. By improving and miniaturizing the distal end tools (microtools), providing force and tactile feedback, integrating sensors and autonomous steering, and improving imaging (optical and ultrasound); this very powerful medical technology will be made more usable, widespread, and efficient.

Head and neck trauma, stroke, and myocardial infarctions are conditions that require rapid intervention and where intravascular approaches have significant promise over other methods. In addition, intravascular therapy of the coronary and peripheral vessels is a medical procedure that benefits from the rapid, minimally-invasive treatment. To expand the use of these minimally-invasive techniques for the treatment of critical conditions, smart microtools and controls must be developed. Such smart microtools, with sensors to monitor force and surrounding conditions, are necessary to allow for integration with a remote, teleoperable, computerbased system. Research and development programs are being focused so as to demonstrate the feasibility of the smart microtool approach and will include the fabrication and demonstration of microtools that incorporate robot-like steering, feedback controlled micro-actuation mechanisms, and sensors. These efforts will also be directed to improving the imaging ability of the present, commercially-available intravascular imaging systems (optical and ultrasound) using enhanced computer-vision algorithms. These research and development efforts will result in smart intravascular catheter systems for remote therapeutic intervention incorporating distal and proximal steering, actuation, sensing, and therapy directly adaptable to teleoperation. Smart catheter systems, which incorporate distal end navigation, microactuation, tactile sensing, and feedback control, will facilitate surgical procedures performed by field technicians under the remote supervision of trained surgeons.

The present invention is directed to micromachined rudders, cantilever actuators, microvalves, force sensors, and positioning or steering mechanisms for navigation of endovascular guidewires and/or catheters and redirection of flow in blood vessels. The microactuators of this invention may function, for example, as microrudders that utilize the blood flow to alter the direction of the tip of guidewires and/or catheters. Also, by integrating strain sensors and tactile sensors onto the individual microcantilevers, or utilizing the sensors independently, a feedback loop enables navigation to the targeted destination. These strain sensors can also serve as tactile sensors to sense the vessel walls. Another application of this invention in a micro dimensional scale is to use microvalves controlled electrostatically or by SMA films and to use the rudders in lines through underground water pipes or inaccessible passageways or tubes for steering to enhance the ability to inspect and repair remotely.

SUMMARY OF THE INVENTION

It is an object of the present invention to provide an array of microdevices for positioning/steering and/or sensor applications.

A further object of the invention is to provide microactuators and microvalves.

A further object of the invention is to provide navigation means for catheters and the like which utilize blood flow direction for positioning or steering.

A further object of the invention is to provide a catheter steering arrangement utilizing a plurality of microrudders, microactuators or microcantilevers.

Another object of the invention is to provide a microtool with a steering arrangement composed of microcantilevers having a length of 10's to 100's microns and a thickness of a few microns.

Another object of the invention is to provide positioning/steering microdevices fabricated onto catheters/guidewires, etc. for maneuvering them through narrow blood vessels or passageways.

Another object of the invention is to provide microactuators using shape-memory alloy films or electrostatic means for valving, positioning and steering.

Another object of the invention is to provide microactuators using micromachined polycrystalline silicon cantilevers.

Another object of the invention is to provide a tactile sensor using an array of piezoresistive microcantilevers, etc.

Other objects and advantages of the invention will become apparent from the following description and accompanying drawings. Basically, the present invention involves the use of microvalves and microrudders, such as means for providing navigation of a micro-tool through a blood vessel, passageway, water line, or tubing arrangement, etc., as well as strain and tactile sensors using microcantilevers. The navigation is provided by microrudders for redirecting the tip of a tube/wire, and this can be accomplished by a combination of SMA films and microcantilevers. The invention is particularly applicable for guiding microactuators or force sensors for navigation of endovascular guidewires and/or catheters. The microcantilever of the positioning/steering arrangement function as microrudders that utilize blood flow to alter the direction of movement. Also, by integrating strain sensors and tactile strain sensors onto the individual microcantilevers, a feedback loop enables navigation to the targeted destination. These strain sensors can also serve as tactile sensors to sense the vessel walls.

The steering of catheters, for example, by the cantilever microrudders provided by this invention will have a major impact in the interventional radiology fields. An automatic joystick system could be integrated for approaching virtually any part of the human anatomy. Also the redirection of blood flow locally could induce laminar flow where desirable and direct flood flow out of infected and bulging weak portions of the blood vessels. In addition, by the use of the cantilever microrudders the time involved by highly skilled physicians in the steering of guidewires and/or catheters through the bends and turns of human blood vessels, would be greatly reduced.

BRIEF DESCRIPTION OF THE DRAWINGS

The accompanying drawings, which are incorporated into and form a part of the disclosure, illustrate embodiments of the microcantilever sensor and navigation arrangements of the invention and, together with the description, serve to explain the principles of the invention.

FIGS. 3A and 3B illustrate a bending/steering arrangement utilizing shape-memory allow films.

FIG. 4 schematically illustrates a steering mechanism utilizing microcantilever rudders in accordance with the present invention.

DETAILED DESCRIPTION OF THE INVENTION

The pumping of the human heart is a tremendous power source (avg. 5 l/min. for healthy adults) for many interventional applications. This blood flow in most cases is laminar and therefore a loose object with attached microactuator cantilevers could make turns in the blood vessels by creating a partial pressure to one side of the blood flow. On the other hand, a fixed object with the microactuators could deflect the blood flow in controlled directions. The former technique can be used to guide the tip of a catheter and/or guidewire through the bends and turns of the angiogram and simplify the procedure to reach targeted disease areas for therapeutic or diagnostic purposes. The latter technique can be used to direct blood flow out of unwanted pockets in the vessels such as aneurysms so that self-healing can take place. The cantilever microrudders or SMA thin films of the present invention enable both of the above-referenced techniques.

For underground pipe lines, it is not always possible to detect leaks, or contamination sources without digging into the affected areas. These procedures are costly and maintenance is almost impossible. If diagnostic lines can be inserted and steered around these underground pipelines, particularly where the flow there through enables the positioning/steering, many applications can be feasible by attaching tools on these remotely operated ground "snakes". The positioning/steering arrangement provided by the cantilever microrudder of this invention can be effectively utilized in such underground pipes or in a tubing arrangement wherein periodic inspection is needed.

In addition to the positioning/steering or bending functions provided by the cantilever microrudders or SMA films, the microcantilevers functions can be integrated with strain sensors and tactile strain sensors, and provide a feedback loop which enables navigation to the targeted destination. These strain sensors can also serve as tactile sensors to sense the vessel walls. Thus, the steering, positioning, bending and sensor functions provided by the microcantilevers will have a major impact in the interventional radiology fields, and can be utilized for inspection, identification, and repair of inaccessible pipe or tubing systems. The term steering as used hereinafter includes positioning and bending operations, which may involve moving an object to the center of a blood vessel, for example, when such is located along one side thereof, and bending an object so as to enable it to go around a curve or bending in the blood vessel, etc., each being in effect a steering type function.

The term cantilever or microcantilever as utilized herein is defined as a device capable of a producing bending motion, the bending of which can be controlled, and thus can function as a microactuator.

Figure 1A:
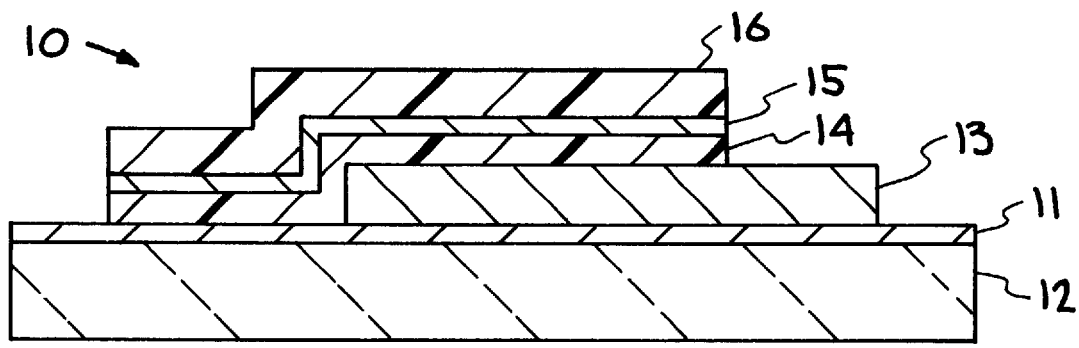
FIGS. 1A and 1B illustrate in cross-section, the fabrication of a conductive polymer based microcantilever.
Figure 1B:
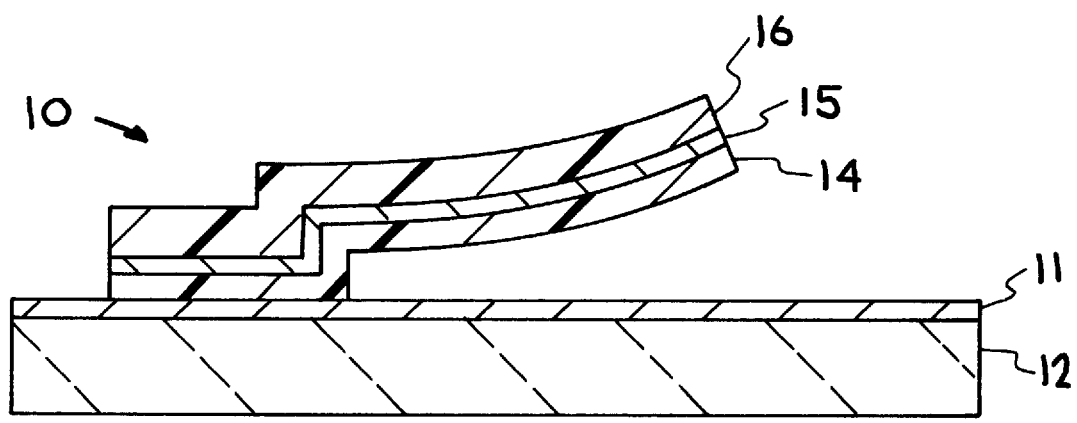

FIGS. 1A and 1B illustrate the fabrication process of an embodiment of a thin film conductive polymer microcantilever for microactuator or micromuscle applications. Conductive polymers are plastic materials which can be rendered electrically conductive when oxidized or reduced by suitable reagents. While conductive polymers have been known for many years and have been widely utilized, it was recently discovered that conductive polymers when used as actuators provide the most similar actuation to muscle contractions. Various types of actuators using conductive polymers with electrochemical doping of donors or acceptors have been developed, and polyimide microcantilevers have been actuated by methods including thermal bimorphs and RF heating. The conductive polymer microfabricated polyimide cantilever as illustrated in FIG. 1B is coated with polypyrrole, which solves many of the problems of the prior known conductive polymer cantilevers. The low power required and large strains available provides advantages over many existing microactivation approaches. Other possible applications include liquid-based microactuators such as micropumps, microvalves, microtweezers, and in vivo microtools.

FIGS. 1A and 1B demonstrate the fabrication sequence and the curling of the cantilever beam, generally indicated at 10, as the results of the tensile residual stress in the polypyrrole. First a thin (500 Å) film 11 of titanium (Ti) is evaporated onto a silicon substrate 12 as an adhesive layer for the polyimide to silicon. A 1 μm aluminum (Al) sacrificial layer 13 is evaporated and patterned on a section of the adhesive layer 11 (substrate 12). A 2.2 μm polyimide structural layer 14 (DuPont PI 2611) is then spun on the remaining section of the adhesive layer 11 (substrate 12) and the sacrificial layer 13, and then fully cured. This type of polyimide was selected due to its low thermal expansion coefficient ($3\times10^{-6}$/° C.). A titanium/gold layer 15 is evaporated on the polyimide layer 14 as the electrode for polypyrrole deposition and doping. A 500 Å nickel (Ni) layer (not shown) is then deposited as a masking layer for reactive ion etching (RIE) of the polyimide layer 14. Then the sacrificial Al layer 13 is etched away as well as the Ni mask. At this point the cantilever beam is free for conductive polymer deposition shown as layer 16. This is done by preparing a deposition solution of 0.1M of pyrrole and 0.1M of tetrabutylammonium p-toluenesulfonate (electrolyte) in an acetonitrile solvent. The pyrrole must be vacuum distilled and stored in a refrigerator. The polypyrrole is then deposited using a Bionanalytical System Instrument (BAS 100) in the cyclic voltammatry (CV) mode. A positive electrode is applied to the microcantilever and the counter electrode is a platinum (Pt) coil. Silver/silver nitrate was used as a reference electrode. About 3 CVs between OV to 1.1V grows approximately 1.2 μm of the conductive polymer 16. The microcantilever 10 as illustrated in FIG. 1B was actuated for 50 cycles and has, for example, a length of 200–500 μm and width of 50–100 μm, and the curling of the cantilever beam is the result of the tensile residual stress in the polypyrrole of the conductive layer 16.

In tests carried out on the FIG. 1B microcantilever, the cantilever was driven dynamically with an AC frequency as high as 1.2Hz and an observed applitude of 50 μm. For maximum stroke movements, the response time was between 1–2 secs./rev. The actuation stress generated was calculated to be at least 50 MPa. Voltages as low as 2–3 volts were applied to generate displacements larger than 100 μm. It was found that for thinner polypyrrole layers (conductive polymer) not only are the stresses larger but the electroluminescence property of the conductive polymer shows a promise as a dynamic electro-optics device. The electromechanical properties make polypyrrole conductive polymers an excellent candidate for artificial micromuscles, since the actuation principle is that of muscle contraction.

Tactile/force feedback sensors for blood vessel navigational feedback control and flow monitoring are being developed. For example, micromachined structures coupled with fiber optic interferometric sensors can measure pressure changes in the surrounding medium. This works by measuring the change in shape of a thin film membrane exposed to the medium. Materials such as piezoelectric films, and other can provide feedback transducers from silicon, or other well designed and characterized microstructures (stress/strain gauges, anenometers, etc.). For example, the embodiment of FIGS. 2A and 2B show a micromachined tactile feedback array sensor, utilizing a plurality of microcantilevers.

By microfabrication and incorporation of micronozzles to the distal end of a catheter, small dose of medicine microparticles, cells can be injected accurately at specific affected areas to provide local precise therapy. Micronozzles (250 μm long, 100 μm diameter with a nozzle orifice of 50 μm) have been fabricated. Such micronozzles can be fabrication in a micromold such as described and claimed in copending U.S. application Ser. No. 08/533,425, filed Sep. 25, 1995, entitled "Polymer Micromold and Fabrication Process", assigned to the same assignee.

Feedback control and signal processing of these micromachined devices is a fairly straight forward task. For example, there is a measurable change in resistivity of shape-memory alloy (SMA) films and piezoresistive materials with both temperature and deformation. From these, device bending or forces can be extracted, amplified, and fed into a feedback circuit. Coupled with computer interfacing and control, one will be able to accurately control the microdevice actuation. Efforts are ongoing to integrate micro sensors/actuators with catheters and guidewires.

Figure 2A:
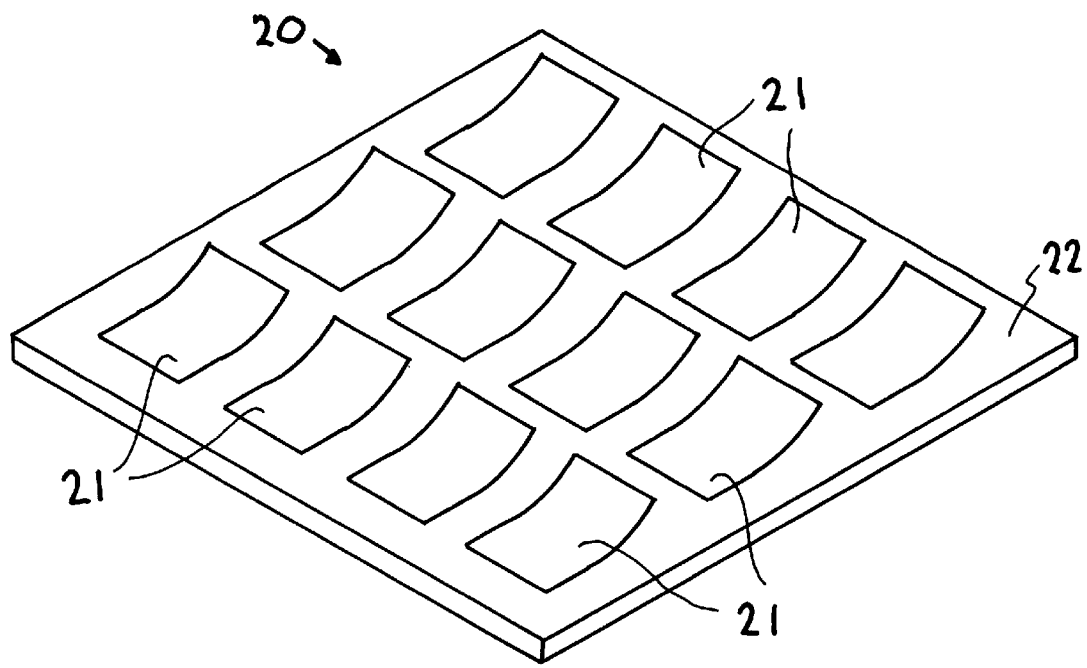
FIG. 2A illustrates a tactile feedback sensor array utilizing microcantilevers, which additionally function for steering of the sensor.
Figure 2B:
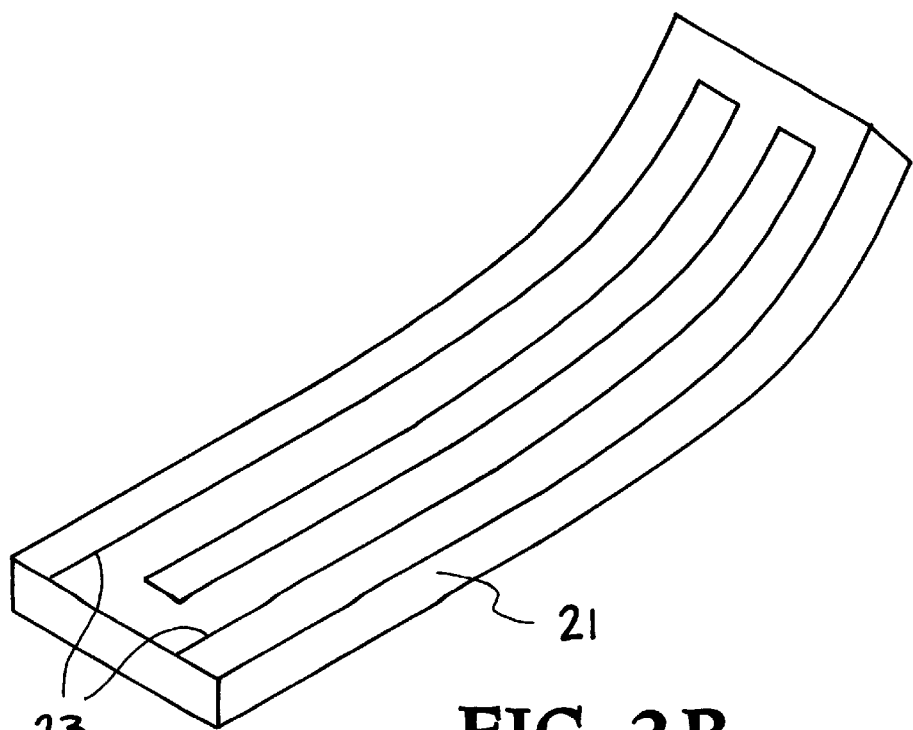
FIG. 2B is an enlarged view of one of the microcantilevers of FIG. 2A.

FIG. 2A is a tactile sensor array that can be mounted on a catheter or guidewire tip for navigation and tissue identification. The FIG. 2A sensor uses micromachined cantilevers with piezoresistive polycrystalline silicon lines for deflection detection, as seen in FIG. 2B which is a greatly enlarged view of a microcantilever of the FIG. 2A array. While not shown, the FIG. 2A tactile sensor array would be coated with a polymer for electrical and mechanical protection.

Figure 7:
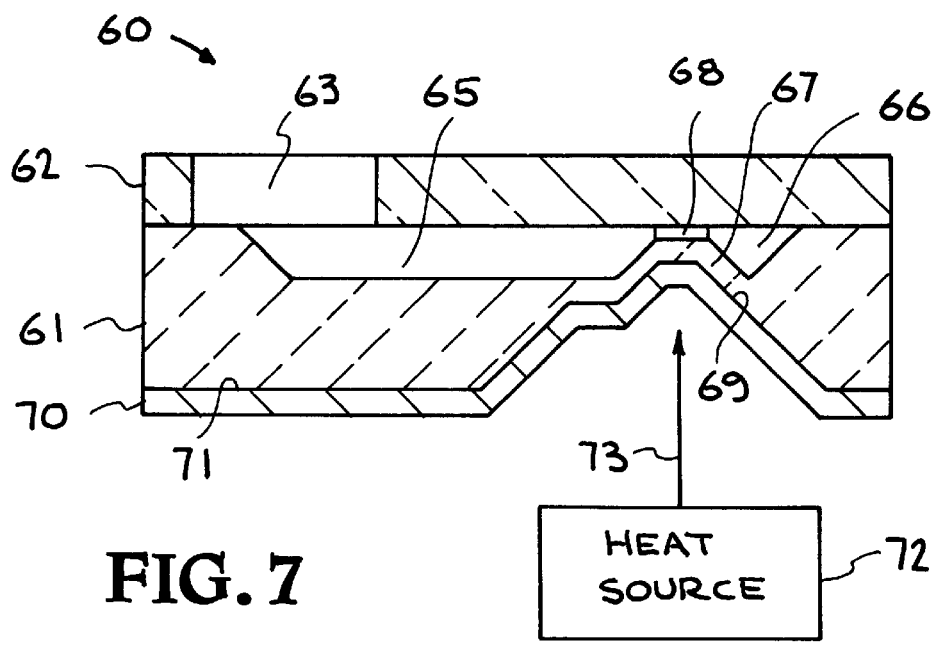
FIG. 7 is a cross-sectional view of the FIG. 6 microvalve taken along the line 7—7.

Referring now to FIGS. 2A and 2B, the tactile sensor array, generally indicated at 20, is composed of a plurality (12 shown) of micromachined cantilevers 21 on a substrate 22, which for example may be constructed of silicon have a width of 20–300 μm, a length of 50–1000 μm, and thickness of 1–20 μm. Each of the cantilevers 21, see FIG. 7, is constructed of silicon, micromachined with an internal stress gradient, and is provided with piezoresistive polycrystalline silicon lines 23 for deflection detection. While not shown the sensor array 20 is coated with a polymer, such as polyimide, or silicone, for electrical and mechanical protection.

By way of example, each of the microcantilevers 21 has a length of 500 μm, width of 50 μm, and thickness of 4 μm. The piezoresistive polycrystalline silicon lines 23 have a width of 2 μm, length of 400 μm, and depth of 1–2 μm; and are spaced apart by a distance of 5 μm, but the parameters depend on the desired resistivity.

The tactile sensor array of FIGS. 2A–2B is fabricated by patterning a doped polysilicon onto the cantilevers, which would be polyimide or silicon, for example.

Research and development is also going forward in the area of catheter steering, positioning, and selective cutting for tissue identification. For example, Seam X Corporation has developed such a system. Coupling this with computer-feedback, joy-stick or automatic steering can be accomplished. This technology has been demonstrated on a larger scale (20 F catheters), and development is going forward to miniaturize the system. Seam X Corporation has also developed autonomous selective cutting (of pipes), sensor technology, data acquisition, and artificial intelligence software. Artificial intelligence software using sensory input and pattern recognition algorithms can differentiate unhealthy target tissue from healthy tissue in real time. The position of the catheter tip is constantly adjusted to address the target tissue. Now the challenge is to micro-size this technology so as to help steer the laser ablation catheter in blood vessels having diameters as small as 250 μm.

Other catheter steering efforts are also under active development using micromachined devices and actuators as described hereinafter with respect to the approaches illustrated in FIGS. 3A–3B and FIGS. 4–5. The FIGS. 3A–3B illustrate a bending or steering approach using a shape-memory alloy-mechanism, while the FIGS. 4-5 illustrate a steering approach using a microrudder (cantilever) mechanism.

The shape-memory alloy (SMA) film based catheter/guidewire bending or steering mechanism of FIGS. 3A–3B illustrate a muscle/joint type actuation wherein a silicon member or tube 30 having a bendable joint 31 therein is provided with thin (1 to 10 $\mu$m) films 32 and 33 on opposite sides of joint 31. By heating film 33, for example, the film contracts causing bending of the joint 31 and stretching of film 32, as shown in FIG. 3B. Heating of the film 32 would cause bending in the opposite direction. The thin SMA films can de deposited on several sides, allowing addressable bending or steering of the device of FIG. 3A. Thus, the FIGS. 3A–3B is broadly considered to be thermally activated.

By way of example, the SMA films 32 and 33 may be composed of nickel-titanium (Ni-Ti), nickel-titanium-copper (Ni-Ti-Cu), or other appropriate SMA compositions.

Figure 5:
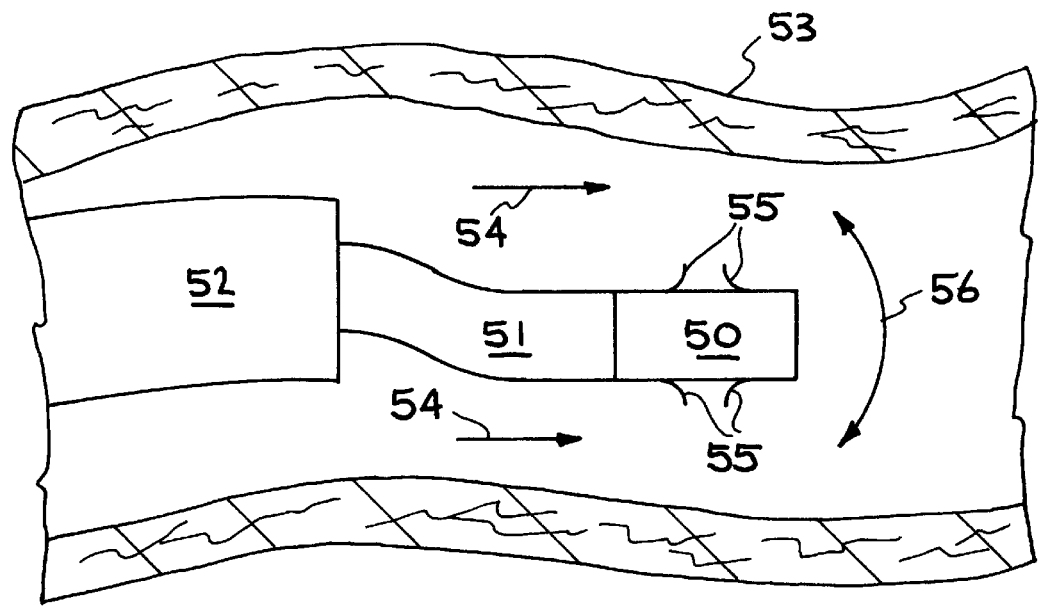
FIG. 5 illustrates a cantilever microrudder steering arrangement for a catheter that uses the flowing blood to help direct the catheter through the blood vessel.

FIGS. 4 and 5 illustrate a microcantilever or microrudder based steering approach, shown generally in FIG. 4, and in a specific catheter attached embodiment in FIG. 5. The plurality of microrudders may be constructed so as to be actuated by thermal bimorph, shape-memory alloy thin films, conductive polymers, piezoelectric, magnetic or electrostatic. By being able to individually control the deflection of the microrudders (microcantilevers), steering becomes available.

As shown in FIG. 4, a catheter or guidewire 40 is provided with four (4) microrudders 41, 42, 43 and 44 for steering the catheter 40 through a blood vessel 45 as indicated by double arrows 46, with blood flow direction being indicated by arrows 47. Depending on the desired steering bend to be made, a particular microrudder (41–44) is activated causing the catheter or guidewire to be steered into blood vessel 48 or blood vessel 49. The microrudders 41–45 may be constructed as cantilevers, bendable joints, microvalves, etc.

Referring now to FIG. 5, a steering tip or mechanism 50 is attached to an end of a guidewire tip 51 of a catheter 52 located in a blood vessel 53 having therein a blood flow direction indicated by legend and arrows 54. Steering tip 50 is provided with four (4) microrudders 55, which, for example may be constructed as described above, and use the flowing blood itself to help direct the catheter through the blood vessel. Activation of one or more of the microrudders 55 cause a defection of tip 50 as indicated by the double arrow 56, such that the tip 50, guidewire tip 51, and catheter 52 are steered through blood vessel 53. Depending on the blood flow direction, and the desired steering bend to be made, a particular microrudder 55 is activated as described above. The dimensions of the microrudders are typically 10's to 100's microns long and only a few microns thick, and can be fabricated using thin film integrated circuit (IC) technology (FIGS. 2A–2B) alone or in combination with SMA thin films (FIG. 3A–3B) or using conductive polymers (FIG. 1A–1B). For a 500 $\mu$m long cantilever, deflections of over 150 $\mu$m can be accomplished.

Figure 6:
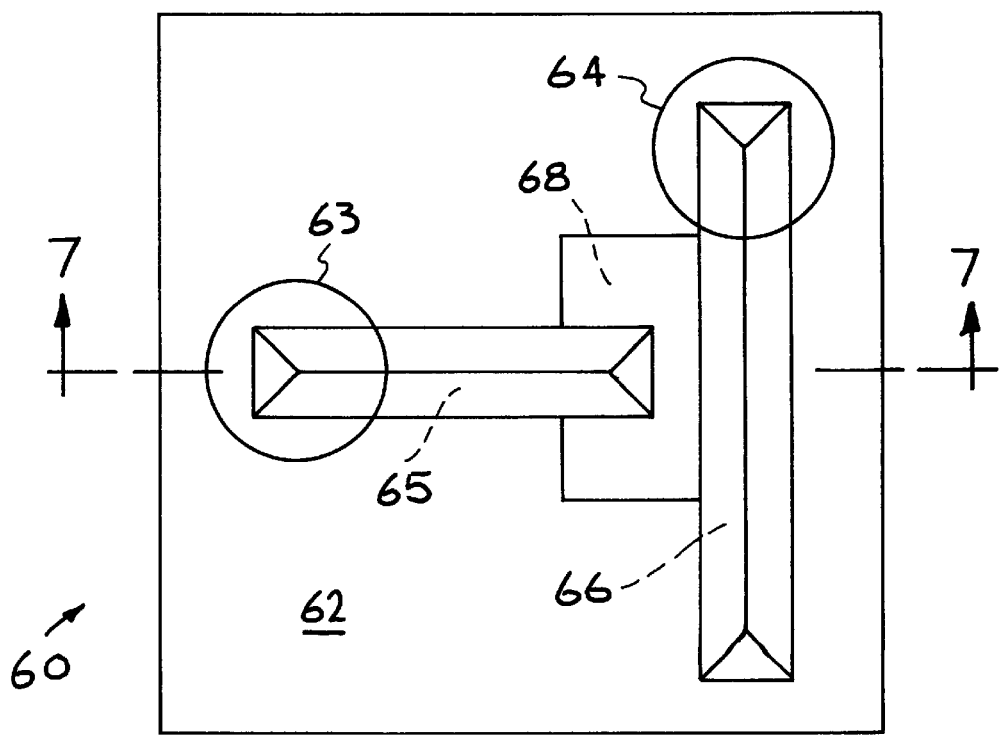
FIG. 6 is a top view of a silicon, SMA activated, microvalve made in accordance with the invention with certain elements shown in phantom.
Figure 8:
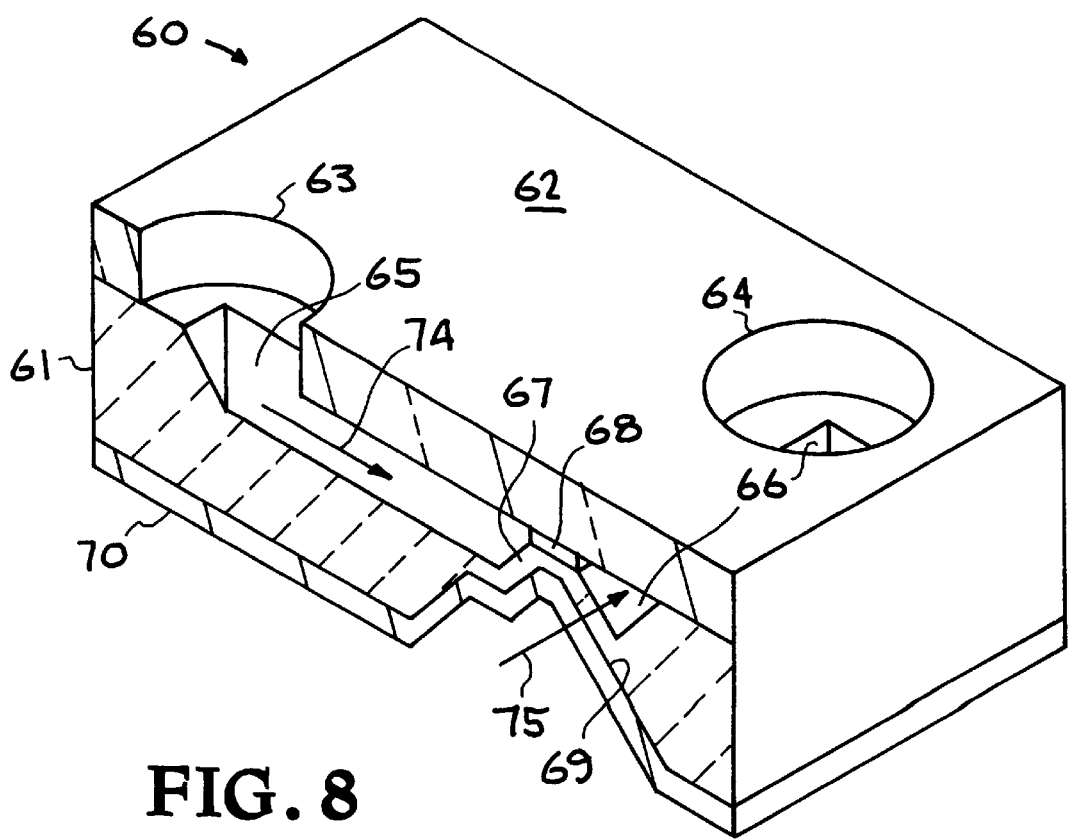
FIG. 8 is a 3D cross-section of the microvalve of FIG. 6.

FIGS. 6 and 7 illustrate an embodiment of a silicon microvalve, made by silicon micromachining, and selective silicon to glass anodic bonding. FIG. 8 is a three-dimensional (3D) cross-section of the microvalve of FIGS. 6 and 7. The microvalve's features include simple processing, processing on one wafer only, normally closed operation, and totally horizontal flow which allows for easy linking of many microvalves to form an array. The microvalve can be actuated by a shape-memory allow (SMA) film deposited on the back side. Heating of the SMA film can be carried out with an integrated resistive heater or an external heat source which causes the SMA film to contract, pulling down on the valve seat (see FIG. 7) and opening the inlet flow channel to the outlet channel (see FIG. 8). With slight variations of the design, the microvalve of FIGS. 6–7 can be actuated magnetically, electrostatically, or using a thermal bimorph.

Referring to FIGS. 6–8, the microvalve generally indicated at 60, comprises a silicon body or member 61 and a glass member or cover plate 62, which are secured together, such as by selective anodic bonding. The glass member 62 is provided with an inlet opening 63 and an outlet opening 64, while silicon member 61 is provided with an inlet channel 65 and an outlet channel 66, with one end of each channel terminating adjacent the inlet opening 63 and the outlet opening 64 of glass member 62. Channels 65 and 66 are normally closed with respect to one another by a valve member 67 formed in silicon member 61 on which is bonded, for example, an $SiO_2$ valve seat 68. Silicon member 61 is thinned as indicated at 69 beneath the valve member 67. A shape memory alloy (SMA) film 70 is deposited on a backside 71 and thinned area 69 of silicon member 61. A heat source 72 is located such as to direct heat as indicated by an arrow 73 towards SMA film 70, causing the film to contract, pulling down the valve member 67 and valve set 68 and opening fluid communication, between inlet channel 65 and outlet channel 66, allowing fluid flow as shown by the arrows 74 and 75 in FIG. 8. By way of example, the SMA film may be a two element alloy, such as Ni-Ti, a three-element alloy, such as Ni-Ti-Cu, or a four-element alloy, such as Ni-Ti-Hf-Cu.

Figure 9:
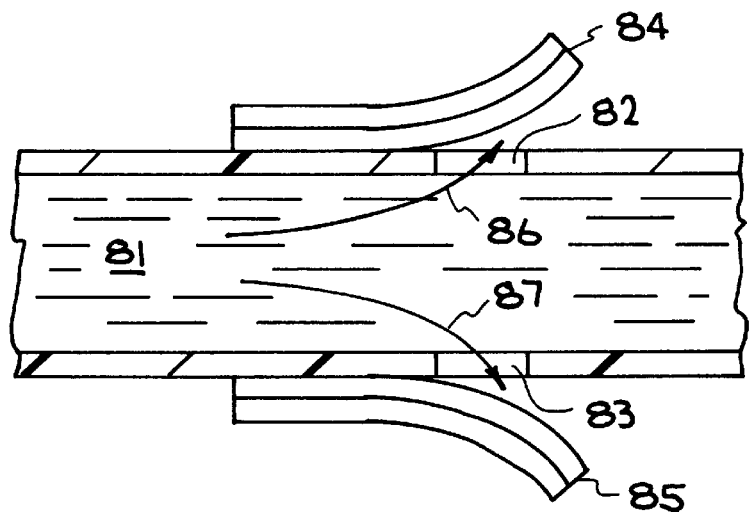
FIG. 9 is a partial cross-sectional view of a microvalve utilizing flow activation.

FIG. 9 illustrates an embodiment of a microvalve wherein the fluid flow may assist in actuation of the valve microactuators or microcantilevers. A tube 80 through which fluid, such as blood 81 passes is provided with a plurality of openings 82 and 83 (only two shown) in the wall surfaces of the tube 80. A pair of microactuators 84 and 85 are secured to tube 80 so as to open and close respective openings 82 and 83. The microactuators 84 and 85 may, for example, be of the type described herein and illustrated in FIGS. 1A–1B, 2A–2B, 3A–3B, or 10A–10B. The difference in the FIG. 9 embodiment is that the microactuators 84 and 85 may be assisted in opening by fluid flow as indicated by arrows 86 and 87. In addition, the microactuators 84 and 85 may function as microrudders for steering the tube 80, with the flow through the openings 82 and 83 determining the direction of movement of tube 80.

Figure 10A:
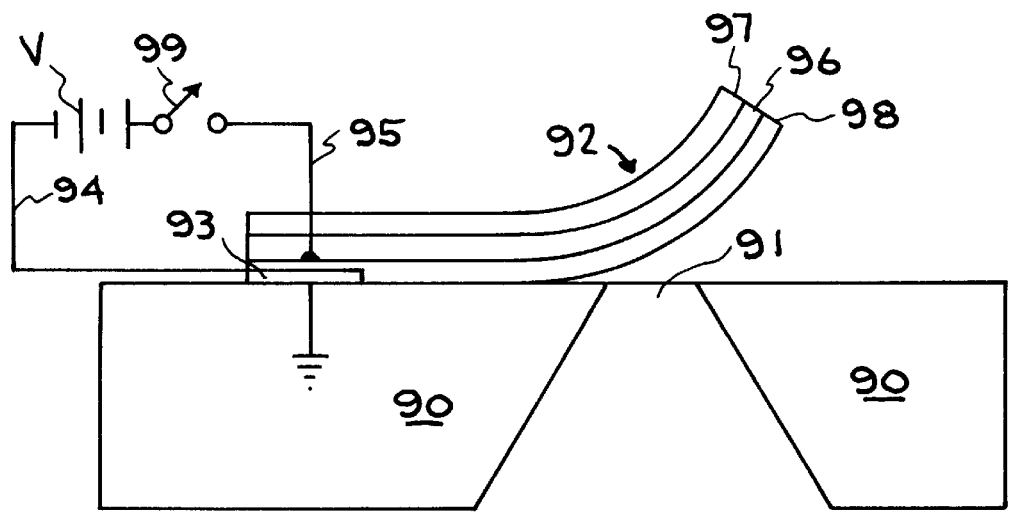
FIGS. 10A and 10B are cross-sectional views of a partial electrostatic microvalve in open and closed positions.
Figure 10B:
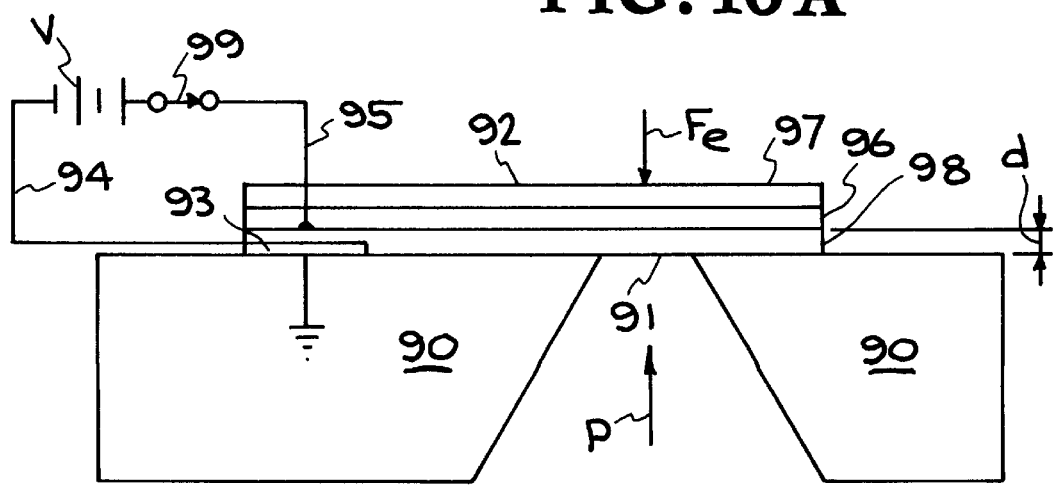

FIGS. 10A and 10B partially illustrate an embodiment of a polyimide bimorph electrostatic microvalve. The microvalve comprises a body 90 having an opening 91 with a microvalve or microactuator mechanism 92, such as described above with respect to FIGS. 1A–1B, secured to the valve body 90. A power supply V is electrically connected to the valve body 90 via a contact or electrode 93 and lead 94 and to the microactuator mechanism 92 via a lead 95 connected to an electrode 96 located between a conductive polymer layer 97 and a layer 98 of polyimide. A switch 99 is located in lead 95, and in its open position, as shown in FIG. 10A the opening 91 in valve body is unclosed (open). Upon closing of the switch 99, current flow causes activation of microactuator 92 thereby closing opening 91, as shown in FIG. 10B. In FIG. 10B, d equals dielectric distance or thickness, Fe equals electrostatic force, and P equals pressure of the fluid.

The polyimide bimorph electrostatic microvalve of FIGS. 10A—10A may be fabricated as follow 1. Dope the surface of a silicon wafer to a resistivity of <10 $\Omega/\gamma$.

2. Coat the silicon wafer with 1000 Å nitride on both sides by LPCVD.
3. Pattern the nitride for ground electrode pads with a mask, and deposit a 3000 Å Al sacrificial layer.
4. Pattern the sacrificial Al layer with a mask, and spin on 1000 Å photoresist, such as PI-2611, and fully cure.
5. Spin on 2 μm of potoresist for lift-off process.
6. Pattern the photoresist with a mask, and evaporate thereon 200 Å Ti followed by 1000° Au, 300 Å Ni and 100 Å Ti.
7. Develop photoresist to complete lift-off process.
8. Spin on 2 μm of PT-2611 (partially cure), roughen with $O_2$ plasma, then spin on 2 μm of PT-2721 or PI-2555, fully cure.
9. Evaporate nickel mask for RIE of polyimide, and backside pattern oxide for back hole etching was a mask, and align to the TiAuNi layers.
10. Using 60° C. KOH, etch through the wafer using one-sided etch fixture (stop on oxide).
11. Pattern nickel with a mask, and etch the nickel in nitric acid.
12. Using $O_2$, RIE in Technics to etch the polyimide layers.
13. Use Pad etchant (ammonium fluoride +HF +$H_2O$) to etch the 1000 Å oxide.
14. Use phosphoric acid at 60° C. to etch Al to release the cantilever, as shown in FIG. 10A.

KOH etches oxide at 75 Å/hour at 40° C., and the etch rate approximately doubles by increasing the temperature 10° C. (i.e. 150 Å/hr. at 50° C.). Using (100) Si, such is etched by KOH at 20 μm/hr. at 65° C. The silicon used were 3 inch wafers, 20.5 mils thick (~520 μm).

By use of computer controlled microactuators, for example, a control/feedback system may be provided. For example, by interconnecting tactile feedback with both the microactuator and the positioning/steering function, and connecting the positioning/steering function and the actuator, a sensor system is set up for controlling the actuator and feeding back movement thereof.

It has thus been shown that the present invention provides microcantilevers for use in valves, actuators and/or sensors for navigation of endovascular guidewires and/or catheters and redirection of flow in blood vessels. The microcantilevers function as steering or bending mechanisms as well as providing flow redirection which can induce laminar flow where desirable and direct blood flow out of infected and bulging weak portions of the blood vessels. The microcantilevers or bending/steering mechanisms of this invention can find applications in underground or non-accessible pipes or tubes.

While particular embodiments, materials, parameters, etc. have been described and or illustrated such are not intended to be limiting. Modifications and changes may become apparent to those skilled in the art, and it is intended that the invention be limited only by the scope of the appended claims.

The invention claimed is:
1. A device adapted for guiding a tool or the like through a passageway, said device comprising:
   a plurality of bendable means; and
   means for individually activating each of said plurality of bendable means.

2. The device of claim 1, wherein said plurality of bendable means comprises a plurality of microcantilevers.
3. The device of claim 2, wherein said means for selectively activating said plurality of microcantilevers is selected from the group consisting of conductive polymers, thermal means, piezoelectric means, electrostatic means, and shape-memory alloy film.
4. The device of claim 1, wherein said activating means for said plurality of bendable means comprises a plurality of shape-memory alloy films.
5. The device of claim 1, wherein said means for selectively activating said plurality bendable means is selected from the group consisting of shape-memory alloy films, conductive polymers, and piezoelectric polycrystalline silicon.
6. The device of claim 1, wherein said plurality of bendable means comprises a plurality of microcantilevers having a length of about 100–500 μm and a deflection capability of under 50 to about 200 μm.
7. The device of claim 6, wherein said activating means for said plurality of microcantilevers comprise at least one shape-memory alloy film.
8. The device of claim 6, wherein said activating means for said plurality of microcantilevers comprise a conductive polymer.
9. The device of claim 8, wherein said conductive polymer includes polypyrrole.
10. The device of claim 6, wherein said activating means for said plurality of microcantilevers, comprise piezoelectric means.
11. Means which may function either as a microactuator or as a force sensor, comprising:
   a substrate;
   said substrate being provided with a plurality of microactuator means; and
   means for activating said plurality of microactuator.
12. The means of claim 11, wherein said microactuator include piezoresistive polycrystalline silicon lines to form a force sensor.
13. The means of claim 11, wherein said microactuator means include piezoelectric polycrystalline silicon lines.
14. The means of claim 11, wherein said microactuator means comprise microcantilevers which include a layer of conductive polymer.
15. The means of claim 14, wherein said layer of conductive polymer includes polypyrrole.
16. The means of claim 11, wherein said microactuator means include at least one shape-memory alloy film.
17. A combination of a device selected from the group consisting of a catheter and a guide wire and the means of claim 11.
18. The steering device of claim 17, wherein said plurality of microdevices includes at least one microcantilever.
19. A steering device for guiding microtools through a passageway having a cross-distance as small as about 250 μm, said steering device comprising:
   a plurality of microdevices positioned in spaced location to each other; and
   means for selectively activating at least one of said plurality of microdevices.
20. The steering device of claim 19, wherein said microdevices include constructed to be directed by a flow of fluid through said passageway.

* * * * *